United States Patent [19]

McNeil et al.

[11] Patent Number: 4,710,165
[45] Date of Patent: Dec. 1, 1987

[54] WEARABLE, VARIABLE RATE SUCTION/COLLECTION DEVICE

[76] Inventors: Charles B. McNeil, 5960 Arbour Ave., Edina, Minn. 55436; Thomas J. McEvoy, 13103 Baker Trail, Minnetonka, Minn. 55343

[21] Appl. No.: 776,633

[22] Filed: Sep. 16, 1985

[51] Int. Cl.$^4$ ................................................ A61M 5/14
[52] U.S. Cl. ........................................ 604/67; 604/31; 604/50
[58] Field of Search ................ 604/67, 50, 31, 66; 417/38

[56] References Cited

U.S. PATENT DOCUMENTS

| | | | |
|---|---|---|---|
| 3,142,298 | 7/1964 | Koshi et al. | 604/31 |
| 3,812,855 | 5/1974 | Banko | 604/31 |
| 3,882,861 | 5/1975 | Kettering et al. | 604/66 |
| 3,918,453 | 11/1975 | Leonard | 604/67 |
| 4,180,074 | 12/1979 | Murry et al. | 604/66 |
| 4,261,360 | 4/1981 | Perez | 604/67 X |
| 4,443,218 | 4/1984 | Decant, Jr. et al. | 604/67 |
| 4,444,545 | 4/1984 | Sanders et al. | 417/38 X |
| 4,468,219 | 8/1984 | Georg et al. | 604/66 |

Primary Examiner—Leo P. Picard
Attorney, Agent, or Firm—Larson and Taylor

[57] ABSTRACT

A compact, lightweight, variable rate suction and collection device is provided for the withdrawal and collection of fluid from a patient. The device includes a collection receptacle which is connected to the patient and to a pump through suction inlet, so that suction is created within the collection receptacle whereby fluids from the patient are drawn into the receptacle. A piezoelectric transducer or diaphragm pressure switch senses the suction created while a suction level selector permits an operator to select a given suction pressure within a predetermined range. A control circuit, responsive to the piezoelectric transducer or switch and to the suction level selector, controls the suction created within the receptacle. Among other features, the control circuit provides a selected suction pressure as well as controls delivery of fractional power to the pump motor to reduce noise. The entire unit including the pump and collection receptacle may be located within a carrying case so that the unit can be worn by a patient or hung at a patient's bedside.

27 Claims, 7 Drawing Figures

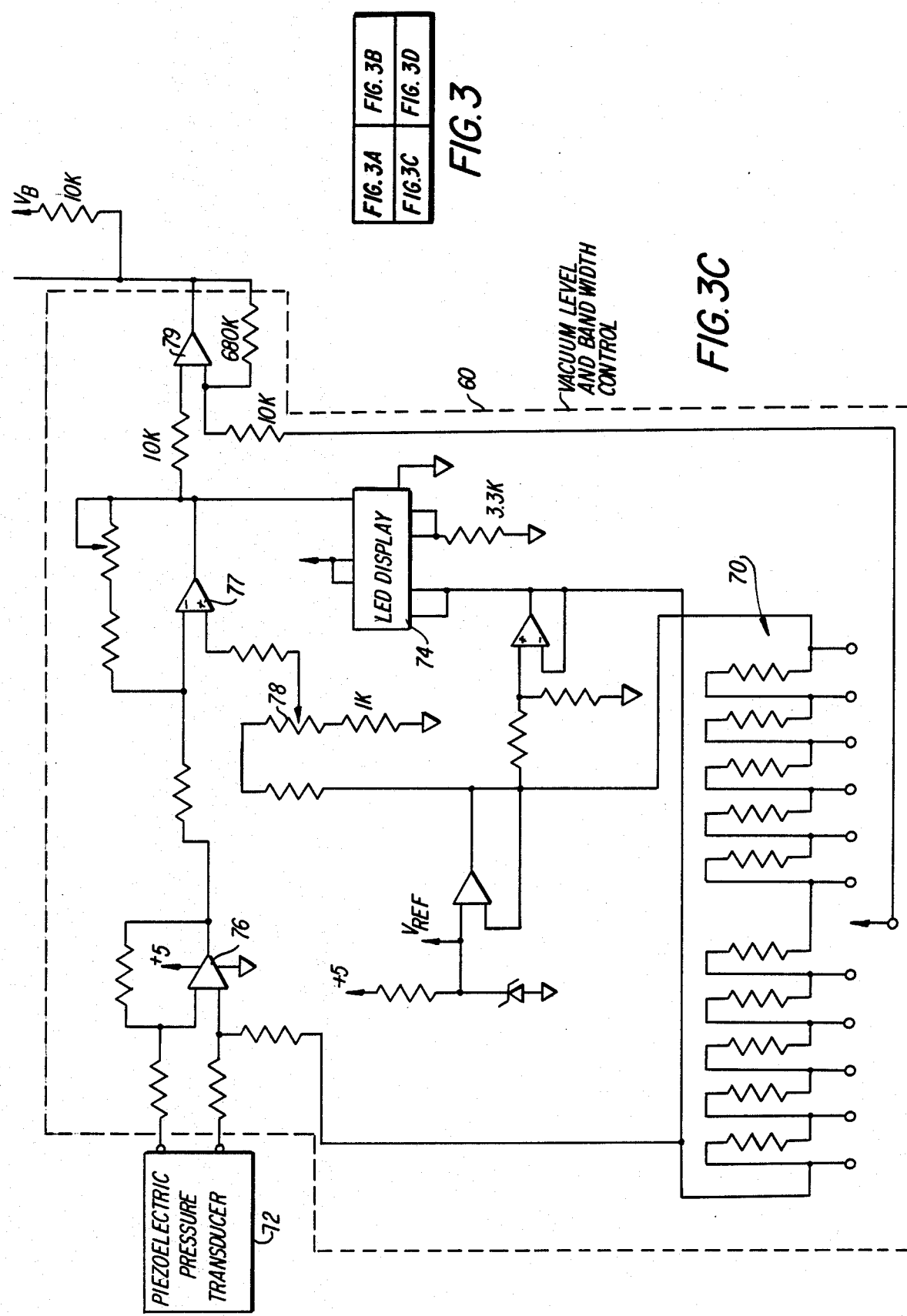

WEARABLE, VARIABLE RATE SUCTION/COLLECTION DEVICE

FIELD OF THE INVENTION

This invention relates generally to devices for draining and collecting fluids by creating a vacuum in a collection chamber which communicates with the source of fluids by a vacuum transmitting connection such as non-collapsing catheters or tubes and more particularly to small, lightweight, wearable, self-contained, variable level suction devices with disposable, closed emptying system.

BACKGROUND OF THE INVENTION

Suction collection systems are commonly employed to drain extraneous fluids, blood, fibrin, blood clots (hematomas), secretions, gastro-intestinal contents and the like from the body. In some postoperative surgical drain applications, suction at levels of 120 mm Hg. to 250 mm Hg. or more may be used. In addition to fluid evacuation, the higher levels of suction are used to provide better fibrin and hematoma or viscous exudate evacuation, to provide internal wound compression, and to promote complete tissue approximation and obliteration of dead space in the surgical wound. The higher levels of suction help prevent clogging of drain systems (a problem commonly associated with low suction wearable devices), and, as stated, help accelerate healing by providing better tissue approximation through internal compression that eliminates dead spaces.

Suction/collection systems are also commonly employed to drain fluids from the esophogus, stomach, and intestinal tract through tubes inserted through either the nasal or oral passages. Suction collection systems are also commonly used for the collection of suctioned materials from lung cavity through thoracic catheters. A more detailed discussion of each of these applications follows.

Closed Wound Suction (C.W.S.) drainage and collection is commonly employed for postoperative drainage of the surgical wound. In C.W.S. drainage the surgeon places a catheter with drain openings (eyes) in the wound site or sites to be drained at the end of the surgical procedure, and secures the drainage catheter to the skin, usually with a suture, at the exit site so that an air tight seal is created in the wound, i.e., a closed wound is created. The proximal end of the drainage catheter is then connected to the suction source. The suction source may be a self-contained wearable, portable device such as described in U.S. Pat. Nos. 3,115,138 (McElvenny) or 4,112,949 (Rosenthal), among others, or provided by a wall suction outlet with or without a suction regulator which receives its vacuum from a central vacuum system in the building. The suction source may also be connected to an A.C. electrical pump such as the Gomco pump. The wall or electric pump systems utilize separate glass or plastic collection bottles or cannisters for collection of the fluids and other materials. These bottles are placed between the suction source and wound catheter and act as a trap to collect the suctioned materials.

Wearable, portable, self-contained disposable suction/collection devices are very popular for C.W.S. applications because they can travel with the patient during patient transport and whenever the patient is away from the bedside such as for radiation therapy or physical therapy. These devices also permit early patient ambulation which assists in early recovery and discharge. These units employ internal metal springs, compressable elastic bulbs, or inflatable latex balloons as the source of suction. Suction levels delivered by these devices generally ranges from 25 mm. Hg. to about 100 mm. Hg., depending on model and manufacturer. Such devices do not provide either a precise level of suction, nor do they deliver a constant level of suction, as the suction level normally drops substantially during the fill cycle.

A number of problems are experienced with these portable, wearable, self-contained suction/collection devices. For example, clogging of the drain eyes and drain system lumen is a frequent problem in certain common applications. This clogging is due to the low and inconsistent levels of suction delivered. Ineffective drainage results from clogged systems and this can lead to infection of the operative site as undrained fluid accumulations and hematomas provide an ideal medium for bacterial proliferation. Further, retrograde infection can result from contamination of the collection reservoir. These collection reservoirs usually become contaminated within 24 to 48 hours with exogenous bacteria because of the frequent opening and reactivation required in attempting to maintain the highest levels of suction. The exogenous bacteria can then proliferate inside the reservoir and migrate through the system into the wound site. In addition, the lack of sufficiently high and constant suction provided may result in less than optimal wound drainage, internal wound compression, elimination of dead space, and tissue approximation. Thus, low suction levels of a declining type as supplied by these units can potentiate infection and retard healing. Because of these problems with the self-contained suction devices, many surgeons employ either wall suction of Gomco type A.C. suction pumps. Wall systems provide suction levels ranging from low levels of 1 to 80 mm Hg. up to maximum levels of 200 mm. Hg. or more.

The Gomco type A.C. vacuum pump systems provide suction levels ranging up to 400 to 500 mm. Hg. or more. The wall suction systems are used more frequently in the hospitals for C.W.S. drainage because wall suction is readily available in most patient rooms in modern hospitals.

There are a number of important advantages of the wall and electrical pump systems over the wearable, self-contained devices. For example, the suction level provided is variable over a range from low to high. Further, the suction level can be set at any desired level, and can be increased to a higher level if problems with clogging occur. In addition, the suction can be temporarily set lower if excessive bleeding should occur. Further, such systems can deliver sufficiently high suction at a relatively constant level to drain effectively without clogging by fibrin or hematoma. The higher suction levels afforded by such systems can provide sufficient internal wound compression to eliminate dead spaces, and can maximize tissue approximation for optimal, rapid wound healing by primary intention without complications such as infection or delayed healing.

The major problem with these systems is that the suction must be disconnected every time a patient is transported, such as during transport from recovery to the patient's room, or when the patient goes for physical or radiation therapy. Further, the patient cannot become ambulatory when the wound is still draining. As mentioned above, early ambulation is highly desirable as it contributes to earlier recovery and discharge. On the other hand, it is undesirable to break the suction because drains without suction or with low levels of suction are prone to poor or ineffective drainage, or complete stoppage by clogging. Breaking the suction system also exposes the system to contamination by exogenous bacteria and retrograde infection.

Wall suction systems are also very imprecise and inaccurate. One hospital system tested with a gauge precalibrated with a mercury manometer delivered 150% higher actual suction levels than the set point on the regulator. Specifically, at a setting of 80 mm. Hg., the system delivered an average of 125 mm. Hg., at a 120 mm. Hg. set point delivered an average of 191 mm. Hg., and at a 200 mm. Hg. delivered 331 mm. Hg. In other hospitals with limited central vacuum capability, the suction level delivered by wall suction can be substantially less than is indicated on the regulator, a condition that will be magnified at peak demand periods. Thus the physician generally cannot know the actual level of suction being delivered with wall systems, because this level varies from regulator to regulator in a hospital, and from hospital to hospital Pleural (chest) drainage is a special type of C.W.S. drainage. Since the lung will collapse if atmospheric pressure is allowed to enter the pleural cavity such as through a post operative drainage catheter, a special suction draining system employing a water seal located between the catheter and the suction source is most commonly used. The water/seal collection unit is attached to an A.C. electrical pump or to wall suction at low levels of suction.

Sump suction systems are those systems that provide one or more air inlet channels (lumens) in the tube or catheter system, combined with a suction lumen to be connected to a suction source such as wall suction or an A.C. Gomco type pump. The objective of the sump system is to provide a suction release in event that soft tissue seals off the openings in the catheter or tube tip. Air enters the system, and prevents tissue from invaginating into the eyes with resultant tissue damage. Sump suction drain tubes are most commonly used in nasogastric tubes to drain the stomach. Surgical sump drains are mainly used in abdominal procedures.

One of the major problems with these systems is that they must be broken whenever the patient is being transported or moved, as described with regard to wall and machine systems for C.W.S. drainage. These systems then may become clogged and require irrigation which may or may not clear the catheter. Portable, self-contained suction devices cannot be employed as they simply suck in air from the air inlet and/or volumes of air and exudate suctioned are too great.

A special portable suction pump for pleural drainage for field emergency or for use while a patient is being transported to the hospital is described in U.S. Pat. No. 4,306,558 (Kurtz). This system controls vacuum through a bleed valve which requires continuous motor operation and battery draw. A manual pump is included so that the unit is still operable in event the battery power or electrical pump failure.

SUMMARY OF THE INVENTION

In all of the applications for suction devices described above, there exists a need for a self-contained, small, lightweight, portable, wearable suction collection device that will provide the desired levels of suction at constant, precise, known levels, to meet the requirements for each application. One object of the invention is to provide a device that combines the self-contained, portable, wearable features of prior art devices, such that of the McElvenny patent referred above, with the best feature of wall and A.C. pump systems, viz., the provision of variable level suction over a range of low to high. An additional object to provide more accurate, precise suction levels over the range desired by practioners, and to provide a system which is easily managed by personnel including the patient, which enables early ambulation of the patient, as well as use when patient is away from the bedside, and which permits patient discharge with the device remaining in use.

In accordance with the present invention, a self-contained, small, lightweight, wearable suction/collection device is provided that will deliver precise, variable rates of suction over any range from 25 mm. Hg. to 250 mm. Hg. or more. This device can be used for closed wound suction drainage, for pleural drainage, for sump tube drainage and for numerous other suction collection applications where a small self-contained device is desired. Further, important features include the an intermittent suction capability, an AC recharge with concurrent operation, and the provisions of alarms for indicating filled container, tipped container and low battery level conditions. The basic components of the unit invention, in addition to the collection container are a pressure sensitive transducer or switch for sensing the vacuum level, being produced, lightweight batteries, a DC motor, a pump, a solenoid for providing intermittent suction, a check valve to prevent vacuum loss through the pump and a control circuit for control the operation of the unit.

In accordance with one important aspect of the invention a piezoelectric transducer or a diaphragm switch is used as the pressure sensing transducer for controlling the vacuum provided. A piezoelectric transducer permits the use of a low voltage (e.g. 6–12 v volt system) and thus enables the battery weight to be reduced. Further, this transducer, in combination with the electronic control circuitry allows the vacuum level to be controlled at any set point within a predetermined range (typically 0 mm to −250 mm. Hg.), with any desired band width around the set point. Further very important features include the provision of fractional power to pump motor to reduce noise and the provision of a spike voltage for motor start-up at hign vacuum levels.

Other features and advantages will be set forth in or apparent from the detailed description of the preferred embodiments which follows.

DESCRIPTION OF THE PREFERRED EMBODIMENTS

Figure 2:
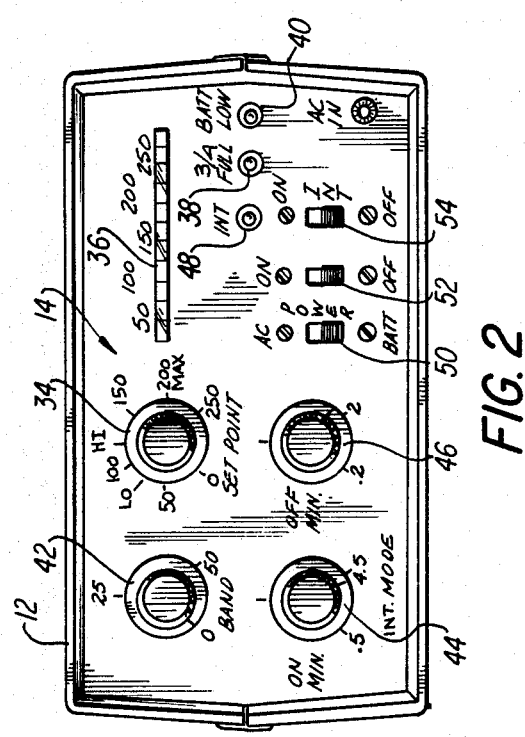
FIG. 2 is a front elevational view drawn to an enlarged scale, of the control panel of FIG. 1.
Figure 1:
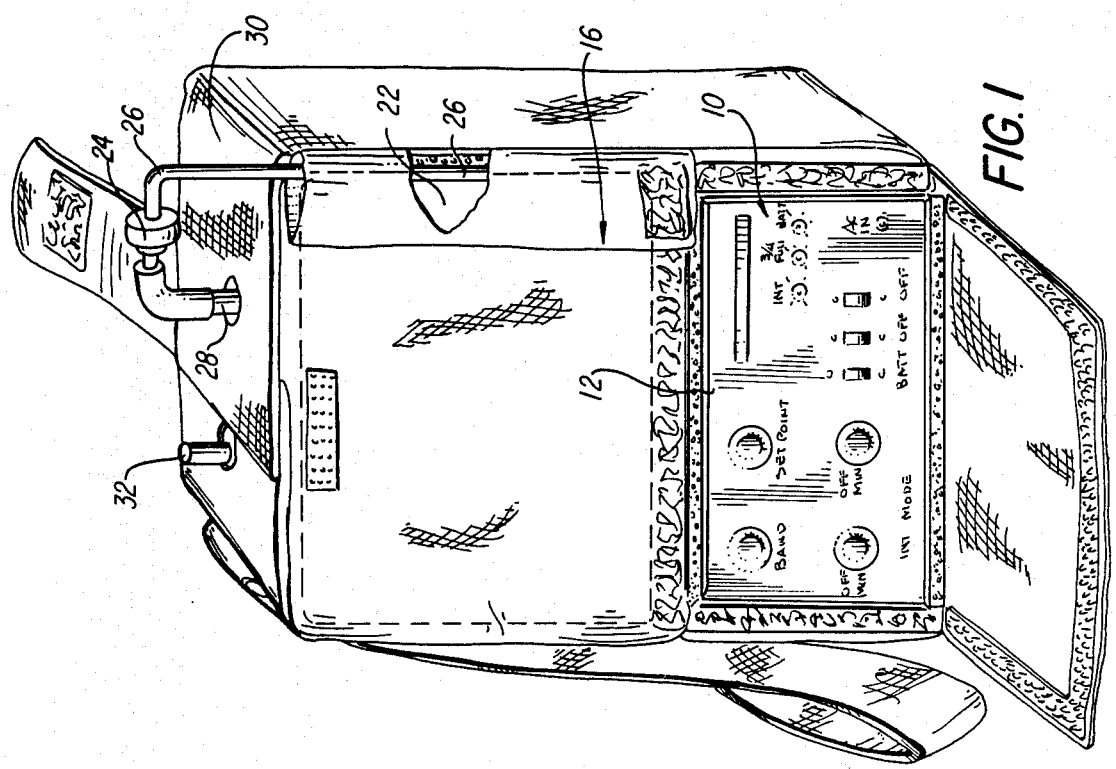
FIG. 1 is a front elevational view of the suction-collection device of the invention with the control panel exposed.

Referring to FIG. 1, a suction/collection device constructed in accordance with one preferred embodiment of the invention is shown. The device includes a vacuum pump, generally denoted 10, and including a pump housing 12 and control panel 14. Control panel 14 is shown in FIG. 2, and is discussed in more detail below. The pump housing 10 is enclosed within a carrying-/hanging case 16 including a carrying strap 18 and a front flap 20 (shown in the open position in FIG. 1) which provides access to control panel 14 without removing case 16. It will be appreciated that the case 16 and pump 10 can also be integral rather than separable.

The pump 10 and the associated vacuum regulation system therefor are connected to a collection receptacle or cannister 22 that is positioned on top of the pump housing 12. This provides an arrangement having a low center of gravity so as to provide maximum stability and to prevent inadvertant tipping. However, it will be understood that in addition to being mounted on the top of pump housing 12, cannister 22 can also be mounted at the side of or beneath the pump unit while still providing good stability, and that a side by side configuration may be preferred for many applications.

A bacterial filter 24 is connected in a line 26 connecting pump 10 and an inlet 28 provided in a cover 30 for the collecting cannister 22 to ensure that the pump 10 will not exhaust any aerosoled bacteria. A "T" connection (not shown) is included in the vacuum line 26 to permit connection of the cannister 22 to wall suction or machine suction if desired. The collection cannister 22 may incorporate a conventional shut-off valve (not shown) which will close off the vacuum line 26 if the unit is tipped or if the unit becomes full. However, this is not required and, for example, the use of a Goretex filter will prevent fluid escape. Activation of this shut-off valve is controlled by a control circuit described below in response to a "full level" sensor (not shown). A "patient" port 32, formed in cover 30 and adapted to be connected to the patient, includes a conventional anti-reflux valve (not shown) for preventing the contents of the cannister 22 from refluxing into the patient line or connection when the cannister is tipped. The collection cannister 22 can also include a bottom emptying port (not shown) with an anti-reflux valve and closure cap. The patient inlet port arrangement is designed to accept the smallest drains via step-up connectors through standard connecting tubes of 3/16" to 9/32" I.D.

The carrying case 16 which contains pump 10 and cannister 20 can be worn by a patient using shoulder strap 18 or by a belt or other attachment arrangement. The case 16 can be readily hung from a bed, stretcher or wheelchair. The case 16 is made from plastic or a fabric material and is designed so that the contents of cannister 22 are easily visible and, with flap 20 down as shown, so that instrument panel 14 can be clearly seen at all times. As stated above, an integral case can also be used and is preferred in many applications.

Referring to FIG. 2, control panel 20 includes a single control knob 34 for turning the unit on and setting the desired suction level. Additional controls which are included are a LED bar display 36 for indicating suction provided in the system; a "Full" indicator audible alarm (not shown) and indicator light 38, a "Low Battery" audible alarm (not shown) and light 40 and, suction dead band width control knob 42, the dead band being typically set at 10 mm Hg. Intermittent operation is also provided for as described below, with a timing control knob 44 for the "On" time, and a timing control knob 46 for the "Off" time. Also included are an intermittent timer with vacuum relief to system, for the "Off" period, and intermittent timing to rest the pump motor at fixed intervals, together with intermittent indicator light 48. A control switch 50 controls switching between A.C. and battery operation, while a further control switch 52 controls whether the power is on or off. An additional control switch 54 controls whether the unit operates continuously or intermittently. In a simplified embodiment, a single on-off switch can be used and such features as the intermittent timing can be omitted. For example, the switches/settings can be limited to an off-on switch, a continuous or intermittent control switch, an open-close control knob or like controller for a vent, a suction level setting, and an A.C. plug receptacle. The controller for the vent preferably includes a solenoid valve (not shown) which vents the collection cannister 22 to atmosphere. The solenoid is de-activated when the system pressure is reduced to zero (atmosphere) and a predetermined time period (e.g. 5 to 10 seconds) elapses in order to conserve battery life.

Figure 3A:
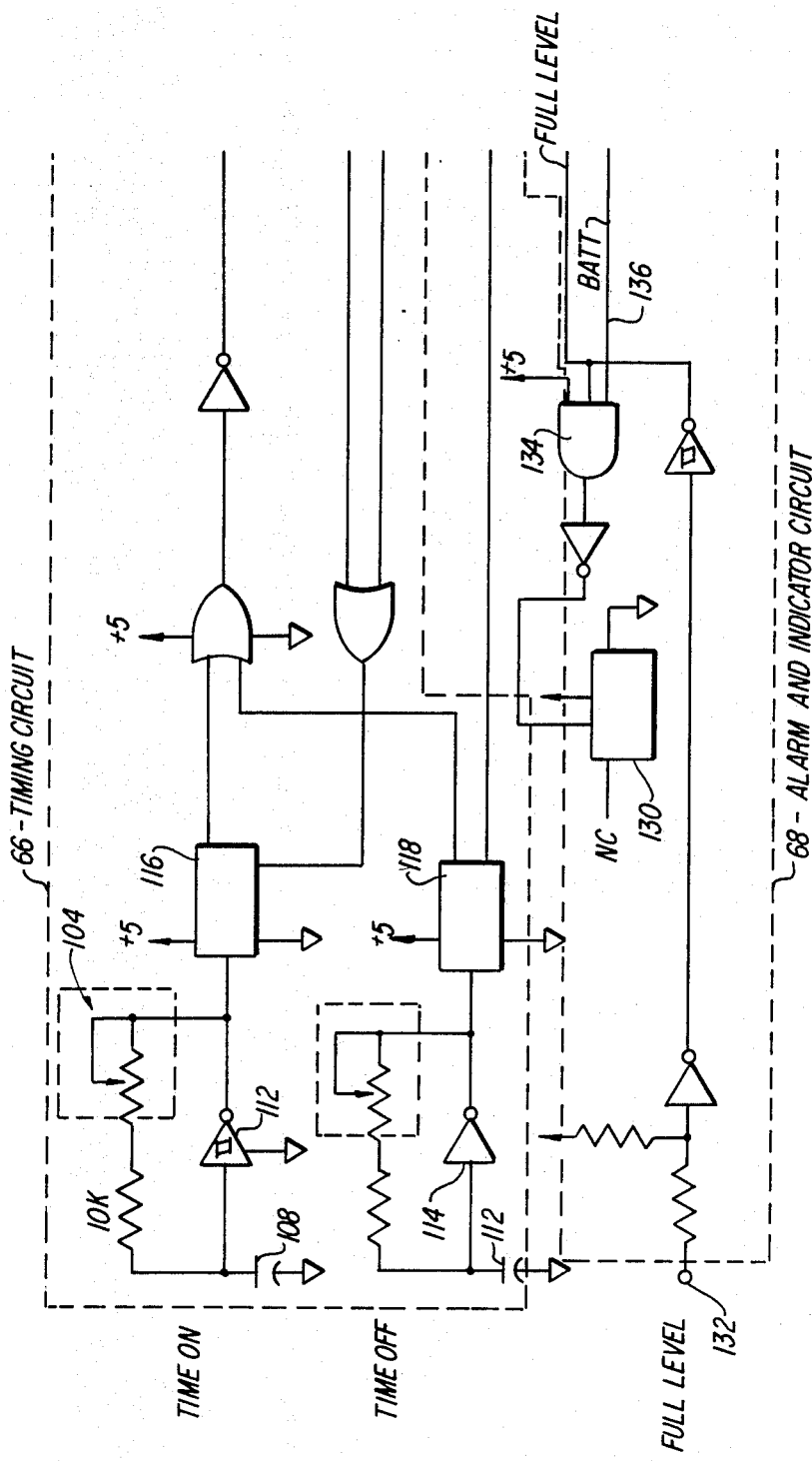
FIG. 3 is a schematic circuit diagram cf the control circuit for the suction-collection device of the invention.
Figure 3B:
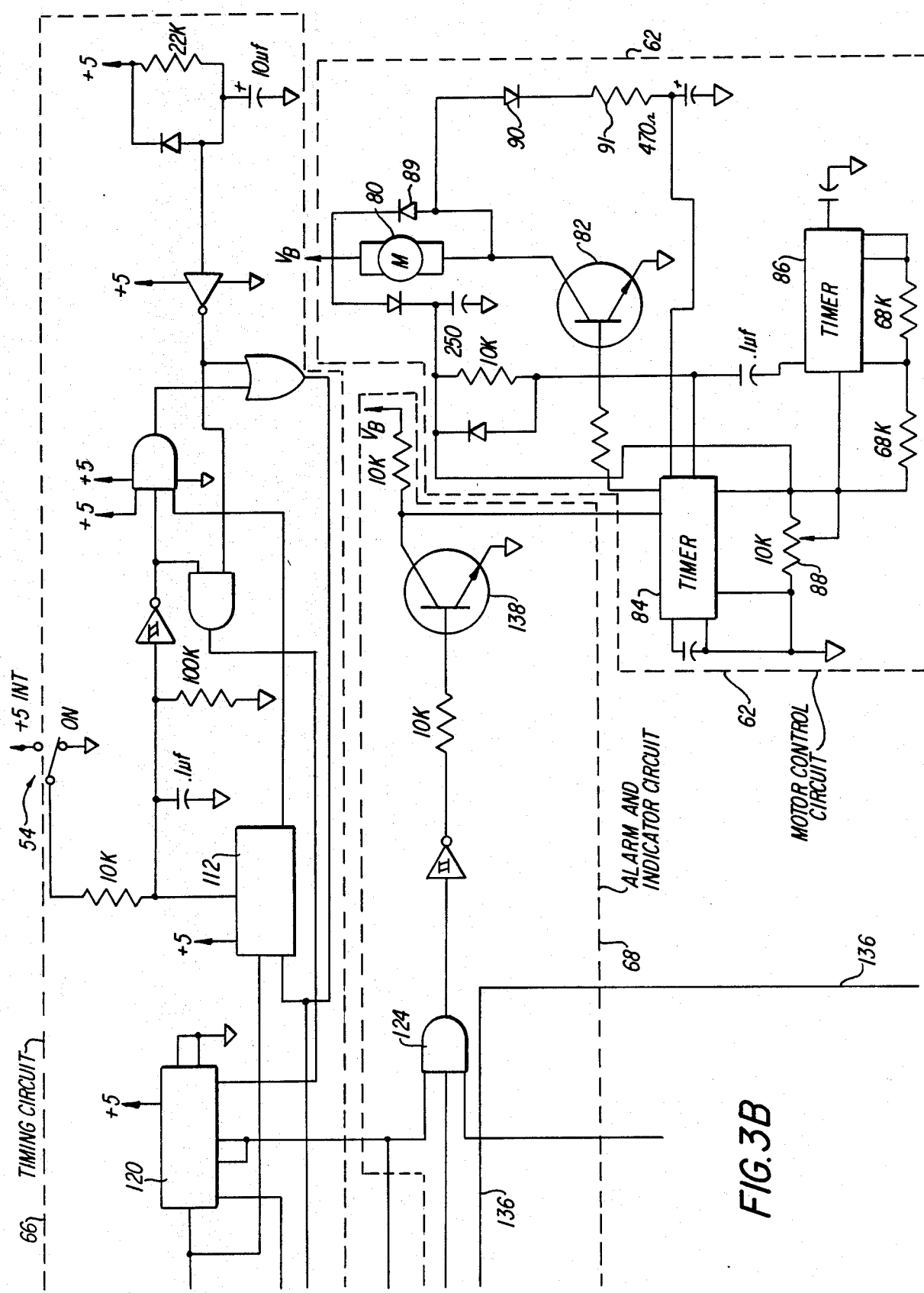
Figure 3D:
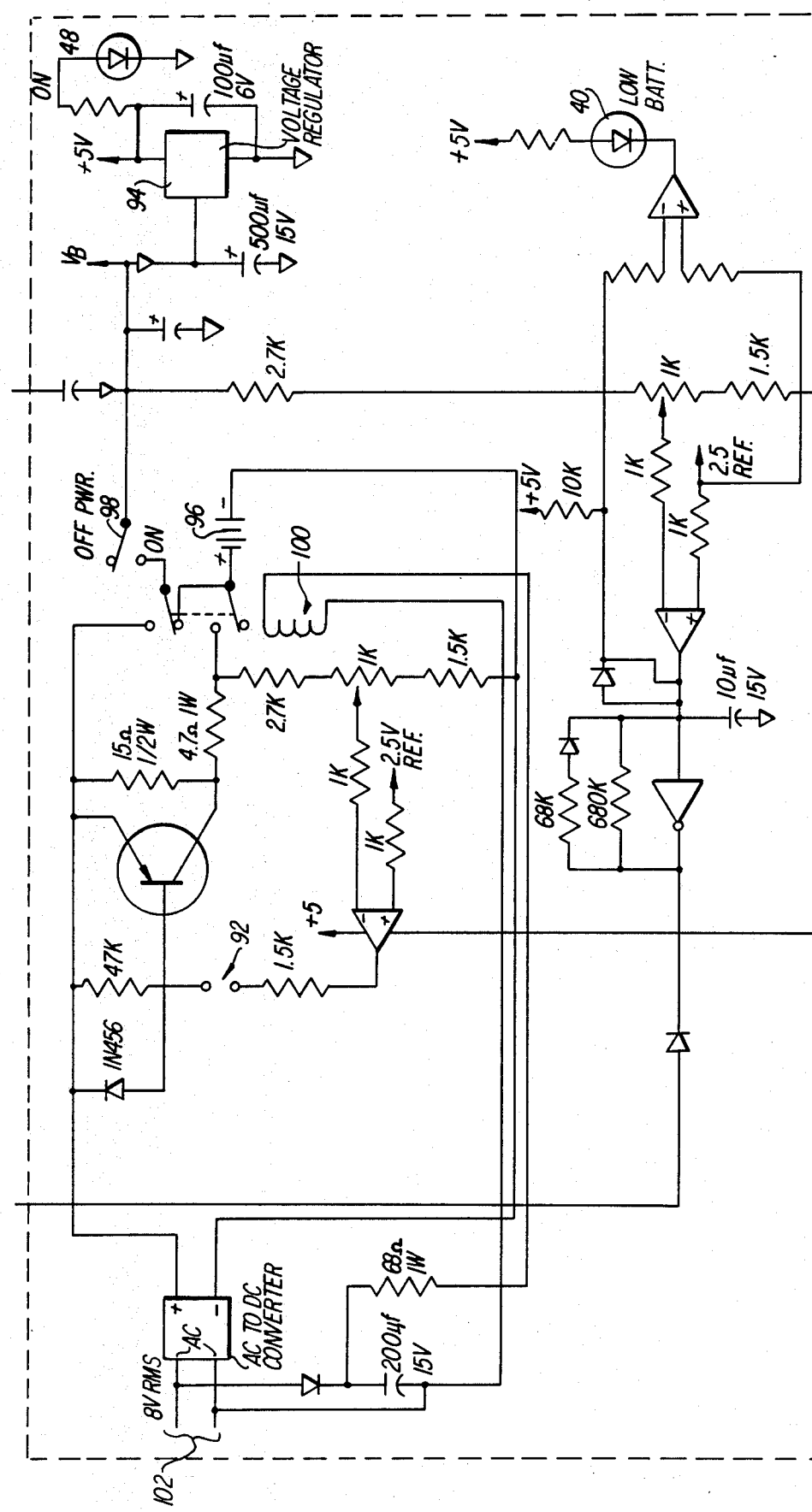

Referring to FIG. 3, the electrical control circuit for the suction and collection device is shown. The control circuit comprises five major units or sections, viz., a vacuum level and band width control section 60, a motor control circuit 62, a power supply 64, a timing circuit 66 and an alarm and indicator section 68. The individual circuit components of the control circuit are connected as shown, and representative component values are given in the drawing, as well as the pin numbers and identifying numbers for the more complex chips.

The vacuum level and band width control section 60 functions, as its name implies, to control the vacuum level applied to the collection cannister 22 and to control the band width or range of the suction to be applied. Key components of this section are a slide switch 70 responsive to control knob 34 of the control panel 14 of FIG. 2 for selecting the desired vacuum (suction) level, a piezoelectric pressure transducer 72 for sensing the actual vacuum level, and an LED display circuit 74 which provides the bar display of FIG. 2. The output of piezoelectric pressure transducer 72 is processed by signal processing circuitry including a pair of operational amplifiers 76 and 78 and forms the basic input to the LED display 74. A potentiometer 78 provides an offset provided on each side of the selected set point. The output of transducer 72 also forms as one input of a further output operational amplifier 79 which is connected to alarm and indicator circuit 68. A connection to the switch arm 70a of slide switch 70 forms the other input and the function of the output of operational amplifier 79 will be discussed below.

The motor control section or circuit 62 provides fractional power to the pump motor 80 using pulse width modulation techniques. This circuit provides frequency control of the duty cycle. In general, the duty cycle is initially set at 50% and is increased to 90% when required, although it will be appreciated that the specific value chosen is a matter of choice and the duty cycle can be set at any desired level. The 50% duty cycle provides reduced power consumption and reduced noise levels while the 90% duty cycle provides the power necessary to overcome resistance to start-up. The key components of this circuit are a control transistor 82 the emitter-collector of which is connected to motor 80, a first timing (oscillator) circuit 84 which is connected as a monostable multivibrator and which controls switching of transistor 82, a second timing circuit (oscillator) 86 which is connected as a stable multivibrator and which controls triggering of oscillator 86 and a potentiometer 88 the tap 88a of which is connected as shown to the input of oscillator 86 to set the duty cycle. As mentioned above, the lowest setting of potentiometer 88 provides a 50% duty cycle. A closed loop feedback circuit senses motor overload and controls which duty cycle mode is appropriate. The transition from one mode to other is accomplished smoothly by this feedback loop, which includes diodes 89 and 90 and resistor 91.

The power supply 64 controls the voltage to the pump motor 80 and to other components of the overall circuit including the supply of a constant voltage to the piezoelectric pressure transducer 72. Power supply 64 also controls charging of the batteries for the unit and includes a rapid charge feature for the batteries supplied by "jumper" terminals 92. In particular, by short-circuiting terminals 92 a rapid charge is provided for the system batteries. Advantageously, nickel-cadium (Nicd) batteries are used to reduce weight although, alternatively, Polaroid type non-rechargable batteries can be used in which case, the unit can still be operated using A.C. It will be understood that power supply 64 is merely exemplary and conventional power supplies can be used. Components of interest include voltage regulator 94, the "ON" indicator lamp 48 (corresponding to that shown in FIG. 2), on "BATT LOW" indicator lamp 40 (also corresponding to that shown in FIG. 2), a battery 96, the power control switch 52, (corresponding to that of FIG. 2), a relay 100 and A.C. input terminals 102.

The basic function of the timing section or circuit is to provide either continuous or intermittent operation of the unit, either with manual or automatic control. A pair of variables resistors 104 and 106, controlled respectively by control knobs 44 and 46 of FIG. 2, provide the "time on" and "time off" settings, respectively. Resistors 104 and 106 are connected to respective oscillator circuits which are formed by capacitors 108 and 110 Schmitt triggers 112 and 114, respectively, and which produce output frequencies of 54 to 540 KHZ and 133 to 1.3 KHZ, respectively as indicated. The oscillators are respectively connected to the inputs of a pair of binary counters 116 and 118. The timing circuit also includes a pair of dual, type D, flip-flop circuits 120 and 122. Flip-flop circuit 120 is connected as a divide by two divider while flip-flop 122 is forms part of a logic circuit for implementing the selection of the continuous operating mode or the intermittent operation mode depending on the setting of an intermittent control switch 54. In general, this logic circuit provides appropriate enabling inputs to the "time on" counter 116 and with switch 54 in the "on" position, the logic circuitry produces an enabling control pulse which is applied to the reset input of flip-flop 120. This forces the output of flip-flop 120 into a state wherein a "run" pulse is applied through an AND gate 124 to the reset input of timer (oscillator) 84, and also causes flip-flop 120 to ignore the signal at the clock input derived from the outputs of counters 116 and 118. With switch 54 in the intermittent position, the logic circuitry produces a control pulse of the opposite state which permits the flip-flop 120 to respond to the signal at clock input. This signal provides for intermittent operation of motor 80 as dictated by the settings of control resistors 104 and 106.

The alarm circuit 68 includes a single buzzer 130 for different alarm conditions through the use of frequency oscillators, thereby further reducing the weight and size of the circuit. A "full level" input terminal 132 is connected between a level sensor (not shown) and the buzzer 130 through an AND gate 134 and the buzzer 130 produces a continuous audible tone for full and tipped container conditions. A "battery low" signal provided to buzzer 130 on line 136 through AND gate 134 from the power supply circuit 64 produces an intermittent tone to indicate a low battery voltage condition, in addition to energizing lamp 40 as described below. The "full level" signal from terminal 132 also forms one input to AND gate 124 and thus provides for shutting off of motor 80, through resetting of oscillator 84, during full or tipped container conditions so as to prevent damage and system contamination.

As noted above, a further input to AND gate 124 is provided by flip-flop 120 while an additional input is provided by the output of the vacuum level and control circuit 60, viz., the output of operational amplifier 79. The output of AND gate 124 controls the state of a control transistor 138 which, in turn, controls resetting of timing circuit (oscillator) 84 and thus controls the operation of pump motor 80.

The basic suction-collection unit of the invention can be readily adapted for different uses. In one preferred embodiment, the unit is designed for closed wound suction applications, while in a further preferred embodiment, a general purpose device is provided which combines A.C. and D.C. operation and which permits use with a wide range of suction catheters, drains and in many other suction devices. A third embodiment provides the intermittent suction feature described above.

Considering these embodiments in more detail, closed wound suction unit constructed in accordance with a preferred embodiment employs 6 volt Polaroid wafer batteries that measure $3'' \times 3\frac{5}{8}'' \times 1/16''$, a low amp motor rated at 0.5 Amp or less, a small diaphragm pump capable of delivering suction of $-250$ mm. Hg. or more, with air flow capacity of about 1 liter per minute, and a piezoresistive transducer. This combination provides a very small, lightweight suction pump system which when combined with the control circuitry described above allows the vacuum to be precisely controlled at any set point within the desired range such as zero to $-250$ mm. Hg. or zero to $-350$ mm. Hg. The pump can be a diaphragm, bellows or piston pump, but a diaphragm pump is preferred because of the low cost to manufacture, and because suction levels of 500 mm. Hg. or more are achievable, with quiet operation and long life.

Any suction dead band size can be provided with this system, from zero to 50 mm. Hg. In closed wound suction applications, the pump will operate until the set level is achieved in the system, and will then stop running while the suction pulls exudate into the collection receptacle. The pump will not restart until the suction in the system drops down to the lower limit of the dead band. With a dead band width of 10 mm. Hg., and a suction setting of 200 mm. Hg., the pump would operate until it creates 200 mm. Hg. of vacuum in the system, then stop and not restart until the suction level drops to 190 mm. Hg. The band width can be operator controlled as descrioed above or be of a fixed width, such as 10 mm. Hg. The basic C.W.S. device will have a fixed band width such as 10 mm. Hg. The band width feature provides an automatic leak detection system, as the pump will cycle on and off frequently if a leak is present in the system, and assures that the suction in the system will at all times be within the band width, 10 mm. Hg., of the set point. The provision of such a band width prevents constant on-off cycling that would otherwise be present with a zero band width.

The electronic control circuit described above controls a number of functions and is designed, inter alia, to: (1) provide a constant voltage to the pressure transducer; (2) incorporate the vacuum control setting and on/off control in a single control lever that is positioned in line with the LED bar display (display 36); (3) provide a fixed band width at desired level such as 10 mm. Hg.; (4) use the input signal from the pressure transducer to control the motor/pump to achieve and maintain the desired vacuum; (5) provide fractional power to the motor to reduce noise, and provide a spike voltage for start up at high vacuum; (6) indicate when battery is going to need replacement through the audible alarm and low battery indicator light described above; (7) indicate when the collection canister is full by audible alarm (buzzer 130) and the "FULL LEVEL" canister indicator light (lamp 38) as described above; and (8) provide an input signal for the LED bar display of the vacuum level in the suction collection system.

The C.W.S. unit is a system that will collect exudate in a closed wound suction drain application over the usual drainage period of 3 to 5 days with a single wafer battery pack. In normal use the collection unit will be emptied three times per day; the drains will be removed after three, four or five days, and the maximum total maximum exudate collected over this period will be in the area of 1,000 ml. or less. The battery pack in this system will have sufficient power to empty and reactivate the system three times or more per day for five days or more. Three emptyings and reactivations of suction in the 500 ml. container to 250 mm. Hg. requires less than 1½ minutes of battery operation, which for five days requires 7½ minutes of battery power. This system provides for a minimum of 30 minutes of power operating at maximum suction levels, and 30 minutes of power provides for 60 reactivations of the 500 ml. container. It will be understood that even more reactivations will be provided for a 400 ml container, or any smaller size, because the smaller the container, the quicker the unit will achieve the vacuum set point. This system design provides adequate excess battery power to accomodate higher than normal rates of emptying and reactivation, or longer than normal periods of drainage in closed wound suction applications. In event that the power of the battery is completely discharged, the battery pack is replaceable with a new pack.

A preferred embodiment of the general purpose D.C./A.C. suction pump unit employs a rechargable NiCad oattery system for use of the unit where A.C. power is not available. The unit converts to A.C. power with a simultaneous recharge when A.C. power is available, and preferred or required for recharging. The NiCad battery pack will provide adequate power for operation of the pump when battery operation is required, such as for patient transport from recovery room to bedside, or for movement to and from therapy departments, or for patient ambulation or discharge. The pump will seldom be required to run continuously, but in event that the pump must do so, the unit will have sufficient power for nearly two hours of running time. Common applications for the general purpose model are closed wound suction drainage, sump suction drainage and thoracic (chest) drainage.

In C.W.S. drain applications, the pump will operate for short intervals in the same manner as described above for the basic C.W.S. unit. However, if an air leak should develop in the system, such as in an air fistula between the drain and the pharynx in neck surgery, the pump would operate frequently or continuously to maintain suction in the system. Under such continuous operating conditions the pump could run for one and one half hours before the battery would require recharging to maintain continuous suction. Intermittent operation of the pump in the C.W.S. application provides an indication that there is a leak somewhere in the system. Such a leak could occur at the skin exit site of the drain, or in one of the connections, or in the collection container lid to canister seal, or in the patient as in the air fistula in the neck.

The general purpose pump unit is also designed for use with sump drains as indicated above, where one or more air inlet channels are included in the tube or drain to provide a suction release feature when tissue occludes the suction openings at the distal end of the tube or drain. When this occurs, the pump will suction air down the air inlet and back up the suction lumen. When fluids are present, the suction will draw these fluids through the suction lumen into the connection container. Thus, in the sump application, the pump will operate on an intermittent basis whenever fluids are suctioned at a greater rate than they are being formed in the area to be suctioned by the tip of the drain or tube.

This unit can also be used, as stated, in connection with chest drainage to supply low, constant level of suction to chest drainage systems and to permit continual supply of suction so as to afford patient movement and ambulation even with the disposable underwater drain systems in place.

Although the invention has been described relative to presently preferred embodiments thereof, it will be understood by those skilled in the art that variations and modifications can be effected in these preferred embodiments without departing from the scope and spirit of the invention.

We claim:

1. A wearable, variable vacuum level suction and collection device for the withdrawal and collection of fluid from a patient, said device comprising:
   at least one collection receptacle including at least one patient inlet for connection to the patient, a further, suction inlet and an outlet for emptying the receptacle;
   pump means, including a pump connection to said suction inlet, for creating suction within said collection receptacle so that fluids from the patient are drawn into the collection receptacle;
   a bacterial filter, interposed between the pump and the collection receptacle, for filtering air drawn into the suction inlet;
   venting means interposed between the pump and bacterial filter for venting the device;
   a pump motor for driving said pump;
   a battery powered power supply for said pump motor;
   a transducer for sensing the suction created;
   suction level selector means for permitting an operator to select a given suction pressure within a predetermined range; and
   a control circuit, responsive to the transducer and to said suction level selector means, for controlling the suction created within the receptacle over said predetermined range; said control circuit including means for providing a selected suction pressure dead band on both sides of the selected suction pressure which defines an upper pressure limit above which the pump motor is de-energized and a lower pressure limit below which the pump motor is re-energized.

2. A device as claimed in claim 1 wherein said dead band is variable.

3. A device as claimed in claim 1 wherein said dead band is fixed.

4. A device as claimed in claim 1 wherein said dead band is proportional to the suction level.

5. A device as claimed in claim 4 wherein the dead band varies linearly from ±10% at −25 mmHg to ±2.5% at −350 mmHg.

6. A device as claimed on claim 1 further comprising means for providing fractional power to said pump motor.

7. A device as claimed in claim 6 wherein said means for providing fractional power to said pump motor comprises a duty cycle control circuit which controls the on and off periods of the pump motor during a cycle of pump motor operation.

8. A device as claimed in claim 7 wherein said duty cycle control circuit includes means for controlling the duty cycle of the motor operation between a predetermined minimum and a predetermined maximum.

9. A device as claimed in claim 8 wherein said minimum is 50% and said maximum is 90%.

10. A device as claimed in claim 1 further comprising means for providing an intermittent vacuum.

11. A device as claimed in claim 10 wherein said means for providing an intermittent vacuum includes a first controller for controlling the on time of the vacuum and a second controller for controlling the off time of the vacuum.

12. A device as claimed in claim 11 further comprising a controller for providing activation of a solenoid valve for providing venting of the collection receptacle to atmosphere during off time periods with only air filtered by the bacterial filter entering the collection receptacle.

13. A device as claimed in claim 12 wherein said controller deactivates said solenoid valve during said off period responsive to the device pressure being reduced to atmospheric and to a predetermined time period having elapsed.

14. A device as claimed in claim 1 further comprise a single alarm for indicating a plurality of alarm conditions.

15. A device as claimed in claim 14 wherein said alarm conditions include a full or tipped collection receptacle condition and a low battery power condition in said power supply.

16. A device as claimed in claim 1 further comprising means for indicating a full or tipped receptacle condition and for terminating operation of the pump motor under such a condition.

17. A device as claimed in claim 1 further comprising means for enabling A.C. recharging of the power supply which permits simultaneous operation of said pump.

18. A device as claimed in claim 1 wherein a pump housing and said collection receptacle are located within a carrying case.

19. A device as claimed in claim 18 wherein said pump housing includes a control panel and said carrying cas includes means for enabling viewing of the control panel when said pump housing and said collection receptacle are located within said carrying case.

20. A device as claimed in claim 1 wherein said pump and said receptacle are mounted in side by side relationship.

21. A device as claimed in claim 1 further comprising an integral case.

22. A device as claimed in claim 1 further comprising a carrying case for carrying the components of the device; said carrying case including a carrying strap.

23. A device as claimed in claim 1 wherein said battery powered power supply includes NiCad batteries.

24. A device as claimed in claim 1 wherein said battery powered power supply includes 6-volt wafer batteries.

25. A device as claimed in claim 1 further comprising means for providing a spike voltage for starting up of the motor at high vacuum levels.

26. A device as claimed in claim 1 wherein said vent valve means comprises a solenoid for controlling a vent valve capable of manual activation to permit drainage of said collection receptacle with only air filtered by said bacterial filter entering the collection receptacle.

27. A device as claimed in claim 1 further comprising manual valve means interposed between the bacterial filter and the pump.

* * * * *